United States Patent
Lloyd et al.

(10) Patent No.: US 8,585,646 B2
(45) Date of Patent: *Nov. 19, 2013

(54) SYSTEM AND METHOD TO VENT GAS FROM A BODY CAVITY

(75) Inventors: Duane Earl Lloyd, Glasgow, MT (US); Keith A. Roberts, White Bear Lake, MN (US)

(73) Assignee: Lexion Medical, LLC, St. Paul, MN (US)

( * ) Notice: Subject to any disclaimer, the term of this patent is extended or adjusted under 35 U.S.C. 154(b) by 1141 days.

This patent is subject to a terminal disclaimer.

(21) Appl. No.: 12/041,233

(22) Filed: Mar. 3, 2008

(65) Prior Publication Data

US 2009/0221963 A1    Sep. 3, 2009

(51) Int. Cl.
*A61M 1/00*    (2006.01)

(52) U.S. Cl.
USPC .......................................................... 604/119

(58) Field of Classification Search
USPC .............. 600/159, 156; 604/540, 541, 35, 45, 604/119
See application file for complete search history.

(56) References Cited

U.S. PATENT DOCUMENTS

| | | | |
|---|---|---|---|
| 2,423,475 A | 7/1947 | Claude et al. | 128/270 |
| 2,465,357 A | 3/1949 | Correll | 106/122 |
| 2,507,244 A | 5/1950 | Correll | 260/117 |
| 2,602,042 A | 7/1952 | Abbott | 167/84 |
| 3,005,457 A | 10/1961 | Millman | 128/296 |
| 3,122,479 A | 2/1964 | Smith | 167/84 |
| 3,185,355 A | 5/1965 | Lipman | |
| 3,328,250 A | 6/1967 | Mentzer | 167/65 |
| 3,599,639 A * | 8/1971 | Spotz | 604/119 |
| 3,810,473 A | 5/1974 | Cruz et al. | 128/334 |
| 3,813,466 A | 5/1974 | Anderson | 424/28 |
| 4,002,173 A | 1/1977 | Manning et al. | 128/296 |
| 4,144,040 A | 3/1979 | Claes et al. | 55/97 |
| 4,215,200 A | 7/1980 | Miyata et al. | 435/273 |
| 4,273,126 A | 6/1981 | Grane et al. | 604/319 |
| 4,292,972 A | 10/1981 | Pawelchak et al. | 128/296 |
| 4,394,373 A | 7/1983 | Malette et al. | 424/95 |
| 4,439,420 A | 3/1984 | Mattei et al. | 424/78.38 |
| 4,459,139 A | 7/1984 | vonReis et al. | 55/189 |
| 4,671,786 A | 6/1987 | Krug | 604/4 |
| 4,735,603 A | 4/1988 | Goodson | 604/21 |
| 4,822,349 A | 4/1989 | Hursey et al. | 604/367 |
| 5,089,606 A | 2/1992 | Cole et al. | 536/54 |
| 5,098,418 A | 3/1992 | Maitz et al. | 604/319 |

(Continued)

OTHER PUBLICATIONS

PCT Notification of Transmittal of the International Search Report and the Written Opinion of the International Searching Authority, or the Declaration mailed Sep. 18, 2008, re PCT/US07/77960.

(Continued)

*Primary Examiner* — Victoria P Shumate
(74) *Attorney, Agent, or Firm* — Baker Botts L.L.P.

(57) ABSTRACT

One aspect of the invention is a method to vent gas from a body cavity during an endoscopic procedure. A body cavity is in fluid communication with an exhaust gas inlet of a vacuum break device. The vacuum break device has a chamber in fluid communication with both the inlet and an outlet. The chamber may comprise one or more openings in fluid communication with the atmosphere. A conduit in fluid communication with the exhaust gas outlet may be connected directly or indirectly to a suction source. The suction source may be activated.

13 Claims, 2 Drawing Sheets

(56) References Cited

U.S. PATENT DOCUMENTS

| | | | |
|---|---|---|---|
| 5,139,478 A | 8/1992 | Koninckx et al. | 604/26 |
| 5,199,944 A | 4/1993 | Cosmescu | 604/26 |
| 5,284,130 A | 2/1994 | Ratliff | 128/20 |
| 5,290,237 A | 3/1994 | Verkaart | 604/126 |
| 5,336,169 A | 8/1994 | Divilio et al. | 604/22 |
| 5,385,552 A | 1/1995 | Haber et al. | 604/167 |
| 5,409,703 A | 4/1995 | McAnalley et al. | 424/435 |
| 5,578,000 A | 11/1996 | Greff et al. | 604/22 |
| 5,688,256 A | 11/1997 | Surratt et al. | 604/355 |
| 5,707,972 A | 1/1998 | Shimizu | 514/54 |
| 5,722,962 A | 3/1998 | Garcia | 604/264 |
| 5,814,012 A | 9/1998 | Fleenor et al. | 604/26 |
| 5,836,970 A | 11/1998 | Pandit | 606/213 |
| 5,840,777 A | 11/1998 | Eagles et al. | 521/82 |
| 5,849,005 A | 12/1998 | Garrison et al. | 606/1 |
| 5,851,461 A | 12/1998 | Bakis et al. | 264/50 |
| 6,060,461 A | 5/2000 | Drake | 514/54 |
| 6,095,971 A * | 8/2000 | Takahashi | 600/159 |
| 6,110,259 A | 8/2000 | Schultz et al. | 96/273 |
| 6,142,980 A * | 11/2000 | Schalk | 604/247 |
| 6,576,033 B1 | 6/2003 | Booth | 55/485 |
| 6,589,316 B1 | 7/2003 | Schultz et al. | 95/273 |
| 6,592,543 B1 | 7/2003 | Wortrich et al. | 604/35 |
| 6,746,504 B2 | 6/2004 | Booth | 55/485 |
| 6,875,198 B2 | 4/2005 | Foley | 604/119 |
| 6,992,233 B2 | 1/2006 | Drake | 602/48 |
| 7,070,722 B1 | 7/2006 | Gilchrist et al. | 264/50 |
| 7,101,862 B2 | 9/2006 | Cochrum et al. | 514/54 |
| 7,175,612 B2 * | 2/2007 | Felix et al. | 604/323 |
| 2002/0193761 A1 * | 12/2002 | Lord | 604/323 |
| 2003/0073663 A1 | 4/2003 | Wiseman et al. | 514/54 |
| 2003/0183082 A1 | 10/2003 | Schultz et al. | 95/273 |
| 2004/0243043 A1 | 12/2004 | McCarthy et al. | 602/48 |
| 2005/0038369 A1 | 2/2005 | Gregory et al. | 602/48 |
| 2005/0137512 A1 | 6/2005 | Campbell et al. | 602/41 |
| 2005/0147656 A1 | 7/2005 | McCarthy et al. | 424/445 |
| 2006/0036221 A1 | 2/2006 | Watson | 604/319 |
| 2007/0066924 A1 | 3/2007 | Hopman et al. | 602/48 |
| 2007/0137484 A1 | 6/2007 | Roberts | 95/273 |

OTHER PUBLICATIONS

*USPTO, Office Action* dated Dec. 5, 2008 for U.S. Appl. No. 11/733,964, filed Apr. 11, 2007, in the name of Roberts et al, (12 pgs. ), Dec. 5, 2008.

PCT Notification of Transmittal of the International Search Report and the Written Opinion of the International Searching Authority, or the Declaration re: International Application No. PCT/US09/35241, International filed Feb. 26, 2009, mailed Apr. 14, 2009 (9 pages).

Ott, Douglas E., *Smoke Production and Smoke Reduction in Endoscopic Surgery: Preliminary Report*, End. Surg; 1993, No. 4, vol. 1: 230-232 (4 pages), Aug. 1993.

Ott, Douglas E., *Carboxyhemoglobinemia Due to Peritoneal Smoke Absorption from Laser Tissue Combustion at Laparoscopy*, Journal of Clinical Laser Medicine & Surgery, vol. 16, No. 6, 1998, pp. 309-315 (7 pages).

Bhaskara Jasti, et al.; Business Briefing: Pharmatech; *Drug Delivery Polymers: Recent Advances in Mucoadhesive Drug Delivery Systems*; 3 pages, 2003.

Eric M. Acheson, et al.; The Journal of TRAUMA® Injury, Infection, and Critical Care; *Comparison of Hemorrhage Control Agents Applied to Lethal Extremity Arterial Hemorrhages in Swine*; vol. 59, No. 4; pp. 865-875, Oct. 2005.

Roberts, et al., *System and Method to Vent Gas from a Body Cavity*, U.S. Appl. No. 11/733,964, filed Apr. 11, 2007 (US 2008-0082084).

Roberts, et al., *Hemostat Agent and Method*, U.S. Appl. No. 11/861,719, filed Sep. 26, 2007 (US 2008-0076722).

Roberts, et al., *Hemostatic Sponge and Method of Manufacture*, U.S. Appl. No. 61/068,226, filed Mar. 4, 2008.

*USPTO, Office Action* dated Jul. 6, 2009 for U.S. Appl. No. 11/733,964, filed Apr. 11, 2007, in the name of Roberts et al, (11pgs. ), Jul. 6, 2009.

*USPTO, Advisory Action* dated Oct. 5, 2009 for U.S. Appl. No. 11/733,964, filed Apr. 11, 2007, in the name of Roberts et al, (3 pgs. ).

Roberts et al., U.S. Appl. No. 11/733,964, *USPTO Interview Summary*, (4 pgs), Mar. 18, 2009.

Roberts et al., U.S. Appl. No. 11/733,964, Response to Office Action, (12 pgs), Apr. 2, 2009.

Roberts et al., U.S. Appl. No. 11/733,964, Response to Final OA (10 pgs), Sep. 18, 2009.

Roberts et al., U.S. Appl. No. 11/733,964, Notice of Appeal and Pre-Appeal Brief Request for Review (6 pgs), Oct. 6, 2009.

Roberts et al., U.S. Appl. No. 11/733,964, Appeal Brief (33 pgs), Feb. 19, 2010.

Roberts et al., U.S. Appl. No. 11/733,964, *USPTO Examiner's Answer* (12 pgs), May 17, 2010.

Roberts et al., U.S. Appl. No. 11/733,964, Reply Brief (14 pgs), Jul. 14, 2010.

Roberts et al., U.S. Appl. No. 11/733,964, *USPTO Election Restriction* (7 pgs), Aug. 25, 2008.

Roberts et al. , U.S. Appl. No. 11/733,964, Response to OA Containing Election/Restriction Requirement (7 pgs), Sep. 18, 2008.

Roberts et al., U.S. Appl. No. 11/733,964, *USPTO Decision on Appeal* (6 pgs), Apr. 26, 2012.

Roberts et al., U.S. Appl. No. 11/733,964, *USPTO Notice of Allowance and Fee(s) Due* (7 pgs), Sep. 4, 2012.

Roberts et al., U.S. Appl. No. 13/858,601 Divisional Application filed Apr. 8, 2013, *System and Method to Vent Gas from a Body Cavity*.

Roberts et al., U.S. Appl. No. 13/858,601, filed Apr. 8, 2013 USPTO *Notice of Allowance and Fee(s) Due;* Aug. 2, 2013.

* cited by examiner

SYSTEM AND METHOD TO VENT GAS FROM A BODY CAVITY

TECHNICAL FIELD OF THE INVENTION

This invention relates generally to endoscopic surgery and more particularly to a system and method to vent gas from a body cavity.

BACKGROUND OF THE INVENTION

During endoscopic procedures, smoke is often generated when a laser is used, for example, to cut tissue during the surgery. If this smoke is vented from the body cavity undergoing surgery to the atmosphere of the operating room, negative consequences can result for the patient and/or the operating room staff. In addition to foul odors, the smoke and other gases expelled from the abdomen during an endoscopic procedure may contain gases such as carbon monoxide, acryloin, acetonitrile, acrylonitrile, acetylene, alkyl benzenes, benzene, butadiene, butene, creosols, ethane, ethylene, formaldehyde, free radicals, hydrogen cyanide, isobutene, methane, phenol, propene, propylene, pyridene, pyrrole, styrene, toluene, and/or xylene. Some or all of these gases may be expelled from a body cavity in smoke (or otherwise) during an endoscopic procedure. Some of these chemicals may be toxic depending upon the quantity. In addition, some of these chemicals may be carcinogenic. Negative health consequences may result due to inhalation of such gases.

SUMMARY OF THE INVENTION

One aspect of the invention is a method to vent gas from a body cavity during an endoscopic procedure. A body cavity is in fluid communication with an exhaust gas inlet of a vacuum break device. The vacuum break device has a chamber in fluid communication with both the inlet and an outlet. The chamber may comprise one or more openings in fluid communication with the atmosphere. A conduit in fluid communication with the exhaust gas outlet may be connected directly or indirectly to a suction source. The suction source may then be activated. The chamber may have a first valve. The first valve may be operable to at least partially obstruct the one or more openings resulting in an increase in gas flow rate within the first conduit due to increased vacuum pressure within the chamber The invention has several important technical advantages. Embodiments of the invention may have none, some, or all of these advantages without departing from the scope of the invention. The invention may allow the use of existing sources of suction (either wall mounted or portable) used by hospitals. These sources can be used to remove smoke and other gases from a body cavity during an endoscopic procedure. The vacuum break device of the invention may improve patient safety by substantially reducing the likelihood that a suction source will cause suction force to be applied to the patient's organs within the body cavity undergoing the operation. Because the invention may use a suction source, it may substantially reduce the likelihood of any smoke or other gases inside the body cavity from escaping into the environment of the operating room. This advantage decreases the exposure of the patient and operating room staff to potentially harmful gases. Also, embodiments of the invention may cause the smoke and other gases to be drawn out of the body cavity at a slow enough rate such that the operation does not need to be interrupted for re-insufflation of the body cavity.

In some embodiments, a valve may be included that allows a suction force to be selectively applied by a user of the vacuum break device. Such selective application may cause a suction force to be felt inside the body cavity. This force may be used selectively to more rapidly evacuate smoke or other gases from the body cavity when desirable. In some embodiments, the force may be used selectively to remove condensate from a conduit (which may be comprised of one or more pieces) leading from the body cavity to the vacuum break device.

BRIEF DESCRIPTION OF THE DRAWINGS

For a more complete understanding of the present invention and the advantages thereof, reference is now made to the following descriptions taken in conjunction with the accompanying drawings in which.

DETAILED DESCRIPTION OF THE INVENTION

Figure 1:
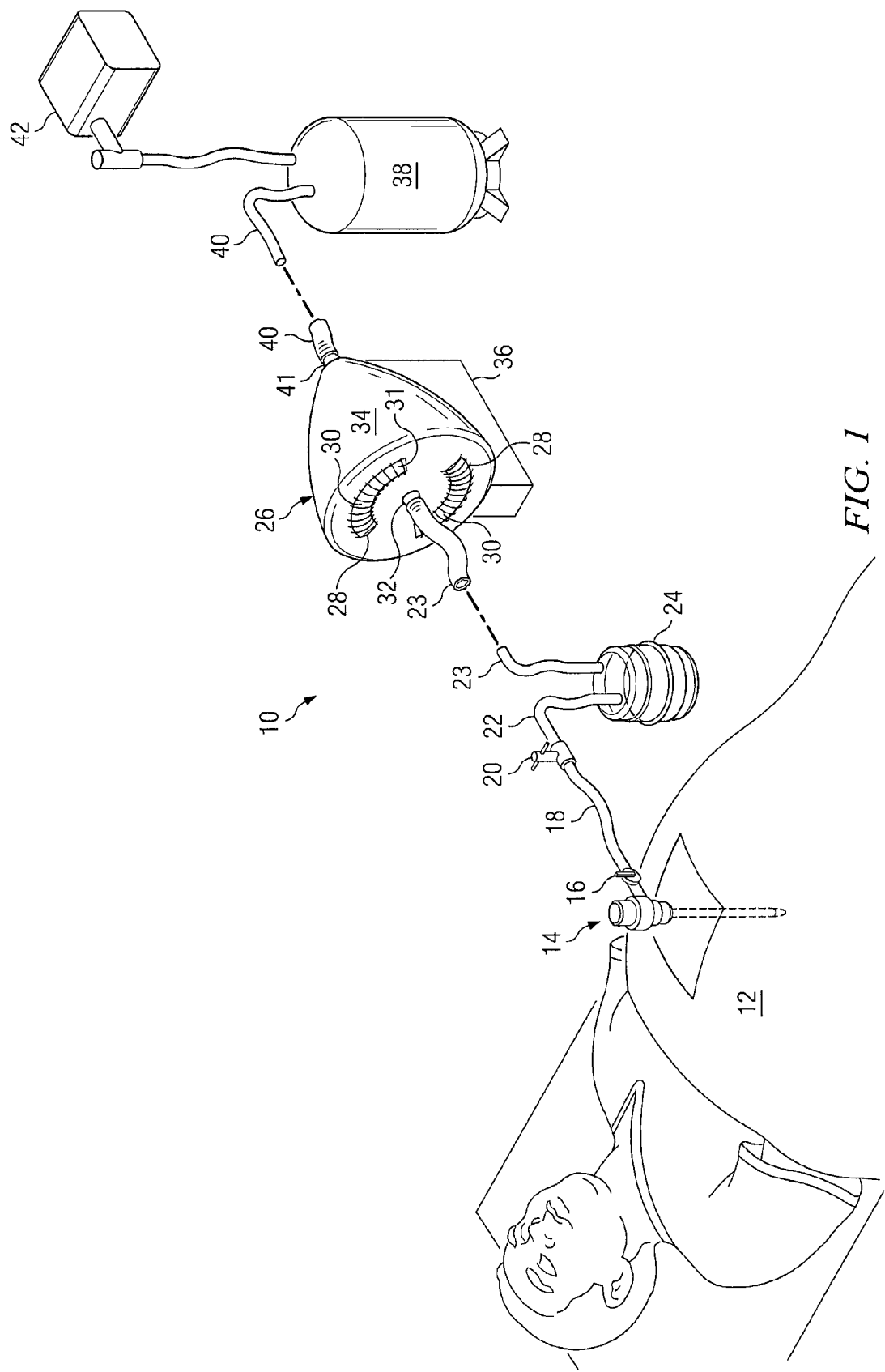
FIG. 1 illustrates one example embodiment of a system to vent gas from a body cavity during an endoscopic procedure.
Figure 2:
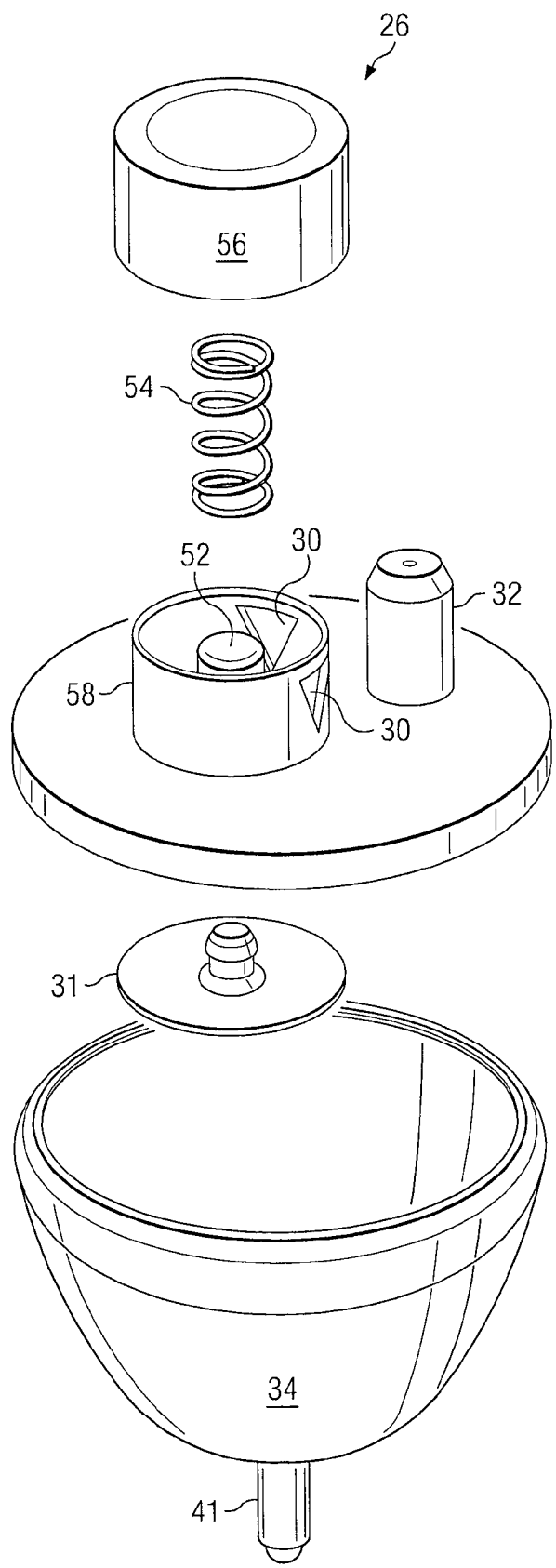
FIG. 2 illustrates a second example embodiment of a vacuum break device that may be used to vent gas from a body cavity during an endoscopic procedure.

The preferred embodiment of the invention and its advantages are best understood by referring to FIGS. 1-2 of the drawings. The embodiments described herein are only example embodiments of the invention and various substitutions and alterations can be made without departing from the scope of the invention.

In some forms of endoscopic surgery (mainly thoracoscopy and laparoscopy, a trocar is used to provide access to a body cavity. Many trocars have a gas conduit in fluid communication with the body cavity that may be used to allow gas to escape from the body cavity. The invention may be used to vent gas from either the thoracic cavity or the peritoneal cavity during an endoscopic procedure. For purposes of this patent, the term "body cavity" refers to either the thoracic cavity or the peritoneal cavity.

FIG. 1 illustrates one embodiment of a system 10 for venting gas from a body cavity during an endoscopic procedure. In the embodiment illustrated in FIG. 1, system 10 comprises trocar 14, valve 20, dessicant chamber 24, vacuum break 26, vacuum canister 38 and suction source 42. Additional components may be included or some of the components illustrated in FIG. 1 excluded without departing from the scope of the invention. In addition, the position of various elements may be changed without departing from the scope of the invention.

System 10 is illustrated in use during a laparoscopic procedure. Trocar 14 is inserted into the peritoneal cavity of patient 12. As illustrated, the patient's abdomen is extended because the peritoneal cavity has been inflated with gas under pressure. As discussed above, the invention may also be used in thoracoscopy. In such an embodiment, trocar 14 may be inserted into the thoracic cavity.

An insufflator (also known as a laparoscopic insufflator) is a device that regulates the flow of gas (most often carbon dioxide) to the body cavity. A laparoscopic insufflator may have a control to allow the surgeon (or other operating room personnel) to set the pressure to be maintained. The insufflator may regulate the abdominal pressure such that a maximum pressure is not exceeded. Exceeding pressure can cause injury to the patient. A laparoscopic insufflator typically also allows a surgeon (or other operating room personnel) to use a control to set the volumetric flow rate of the gas, most typically in liters per minute. By setting a flow rate (typically a maximum flow rate) the surgeon can control how quickly a body cavity is inflated. Controls for pressure and volumetric flow rate such as knobs or buttons are typically included on the panel of the insufflator. In either procedure, an insufflator may be used to supply gas to the body cavity that is inflated for purposes of surgery.

Gas from the insufflator (not explicitly shown) may be provided to a body cavity through trocar 14. In other embodiments, a separate trocar may be used to provide gas to the body cavity. In this embodiment, trocar 14 further comprises a stopcock 16 that may be used to vent gas from the body cavity. When the stopcock is open, gas from the body cavity may flow through the trocar. When the stopcock is closed, gas flow from the body cavity through the stopcock is prevented. In some embodiments, stopcock 16 may allow a variable flow of gas through stopcock 16 depending upon the degree to which stopcock 16 is open. The invention may include trocars 14 without stopcock 16. In addition, embodiments of the invention may have a separate device in fluid communication with the interior of the body cavity that may be used to exhaust gas from the body cavity.

As used herein, the terms "conduit" or "fluid flow path" are meant broadly to refer to one or more structures that allow fluid to flow from one place to another. A conduit or fluid flow path may include a single item, such as a tube between two points. Alternatively, a conduit or fluid flow path may also include multiple items such as multiple tubes and valves between two points. As long as fluid flow is possible through a structure, that structure may be said to be part of or constitute a conduit or fluid flow path between two points.

In this embodiment, the conduit or fluid flow path between trocar 14 and vacuum break 26 comprises tubing 18, valve 20, tubing 22, tubing 23, and dessicant chamber 24. Tubing 18, 22, and/or 23 may be the type of tubing that is typically employed for medical applications. Any type of tubing 18, 22 or 23 can be used without departing from the scope of the invention. In this embodiment, tubing 18, 22 and 23 as well as tubing 40 comprises plasticized PVC tubing but could be any type of tubing. Tubing 18, 22 and 23 may be connected either by sliding the tubing over a ribbed fitting or by including a male or female luer fitting on the tubing to mate with a corresponding male or female luer fitting on trocar 14, valve 20, dessicant chamber 24, and/or vacuum break device 26. Any other type of connector to connect tubing 18, 22 and 23 to the various devices illustrated in FIG. 1 may be used without departing from the scope of the invention. Different types of connectors can be used in different places.

In this embodiment, trocar 14 has a luer fitting to which tubing 18 connects. Trocar 14 may have any other type of connector used to connect trocar 14 to tubing 18 without departing from the scope of the invention. It may also have a ribbed or tapered friction fitting. Tubing 18 may extend between an outlet port on trocar 14 and an inlet port of valve 20.

In this embodiment, valve 20 has an input port and an output port. Valve 20 may be used as an additional mechanism in addition to stopcock 16 to control the flow of smoke and/or other gas from the body cavity to vacuum break device 26. In this embodiment, valve 20 may comprise a stopcock with adjustable flow. In other embodiments, valve 20 may be a pinch valve that slides over tubing 18 such that tubing 18 and tubing 22 are a continuous piece of tubing with a pinch valve slid over the tubing. In other embodiments, valve 20 may simply be replaced by an orifice. The orifice may be inserted into the interior of tubing 18 such that tubing 18 and tubing 22 form a continuous piece with an orifice therein. In other embodiments, the orifice may have an input port and an output port such that it may be connected between tubing 18 and tubing 22. The orifice may be fixed or variable. In addition, a module may be included where various sized orifices may be inserted into the module to control the flow between trocar 14 and vacuum break device 26. The flow between trocar 14 and vacuum break device 26 may also be controlled by choosing tubing of a particular diameter along part or all of the path between trocar 14 and vacuum break device 26. In addition, tubing of a particular diameter may be used alone or in combination with stopcock 16, an orifice or both in order to achieve flow control.

Although in this embodiment valve 20 is illustrated as being between trocar 14 and dessicant chamber 24, valve 20 (or any of the orifice options above) could be placed between dessicant chamber 24 and vacuum break device 26 without departing from the scope of the invention. Valve 20 could be omitted without departing from the scope of the invention. Valve 20 (or any of the orifice options above) could also be placed between vacuum break device 26 and either vacuum canister 38 or suction source 42 without departing from the scope of the invention. In addition, additional valves or orifices of any of the types discussed above could be used in any of the positions discussed above. More than one valve, orifice, or other flow control device could be included at any of the positions described above. For example, in addition to valve 20, a second valve could be inserted between vacuum break device 26 and either vacuum canister 38 or suction source 42. In some embodiments, a valve 20 (or any of the orifice options above) may be included as a part of vacuum break device 26. In most embodiments, valve 20 will be a manually controlled mechanical valve. However, an electromechanical valve 20 could be used in any of the positions discussed above without departing from the scope of the invention.

The fluid flow path between trocar 14 and vacuum break device 26 in this embodiment further comprises dessicant chamber 24. Dessicant chamber 24, as discussed above, may be omitted without departing from the scope of the invention. Dessicant chamber 24 may be connected to tubing 22 and 23 using any of the connection options discussed above. Any connection method may be used without departing from the scope of the invention. Dessicant chamber 24 may be included to absorb moisture from gases expelled from a body cavity of patient 12 during an endoscopic procedure. While any dessicant material can be used without departing from the scope of the invention, activated alumina or silica gel may be suitable for this application.

In this embodiment, dessicant chamber 24 is located prior to vacuum break device 26. However, a dessicant could be included within vacuum break device 26 or dessicant chamber 24 could be placed between vacuum break device 26 and either vacuum canister 38 or suction source 42 without departing from the scope of the invention. As will be discussed later, vacuum break device 26 draws atmospheric air in through openings 30 of vacuum break device 26. Accordingly, placement of dessicant chamber 24 prior to the inlet of vacuum break device 26 advantageously uses the dessicant to remove moisture from the exhausted gas from the body cavity. Placement of the dessicant within the vacuum break device 26 or after vacuum break device 26 may consume the dessicant more quickly because it will then absorb moisture from the atmospheric air that was sucked in through openings 30. Dessicant chamber 24 may be omitted without departing from the scope of the invention. In addition, dessicants may be placed in multiple positions within the fluid conduit or flow path between trocar 14 and suction source 42 without departing from the scope of the invention.

System 10 further comprises vacuum break device 26. Vacuum break device 26 may greatly minimize or eliminate the suction force of suction source 42 on the interior of the body cavity of patient 12 from which gas is being expelled through trocar 14. Because suctional force may damage the organs of the patient 12 within the body cavity, this improvement in patient safety is a significant advance over existing smoke evacuation systems. The vacuum break device has the further advantage, either alone or in combination with valve 20 and/or stopcock 16 of controlling the flow rate of smoke and other gases from the body cavity of patient 12 such that the collapse of the inflated body cavity is minimized or eliminated. For example, in laparoscopic surgery, the peritoneal cavity is inflated by an insufflator to form a pneumo-peritoneum. Smoke evacuation in existing systems during laparoscopic surgery may cause a collapse of the pneumo-peritoneum and thus cause the surgeon to stop operating until pneumo-peritoneum can be restored by the insufflator. The collapse of the pneumo-peritoneum increases the length of the surgery, which may not only be inefficient for the surgeon but may prolong the patient's exposure to anesthetic and other aspects of the surgical procedure. Vacuum break device 26 also advantageously prevents or greatly reduces the amount of smoke and/or other insufflation gas that escapes into the atmosphere of the operating room. In this embodiment, a valve 31 (described in more detail below) is included as a check valve to prevent the flow of smoke and/or other insufflation gas into the operating room when suction force 42 is disabled. The use of suction source 42 to vent smoke and other insufflation gas from the body cavity of patient 12 improves patient safety by greatly reducing or eliminating the release of toxic agents into the atmosphere of the operating room.

In this embodiment, stopcock 16, valve 20, tubing 18, 22 and 23 and/or dessicant chamber 24 may be configured in a manner to control the pressure between the body cavity of the patient 12 and the chamber 34 of vacuum break device 26 to be maintained in the range of one to twenty mm Hg. As discussed above, one or more of these elements may be omitted without departing from the scope of the invention. While other pressure differentials may be maintained without departing from the scope of the invention, the pressure differential may be advantageously maintained within the above range. In addition, the volumetric flow rate of the gas may be maintained into inlet 32 of vacuum break device 26 such that it is between one and twenty liters per minute. In some embodiments, the volumetric flow rate of the gas may be maintained such that it is between one and forty liters per minute because some laparoscopic insufflators are capable of supplying gas at these flow rates through one or more flow channels. In other embodiments, the flow rate may be maintained between 0.5 and 40 liters minute, between 0.5 and 10 liters minute, between 1 and 4 liters per minute, or between 1.5 and 3 liters per minute. Other gas flow rates may be maintained without departing from the scope of the invention. In some embodiments, the surgeon can vary the volumetric flow rate of the gas by adjusting either stopcock 16, valve 20, or both.

Vacuum break device 26 comprises exhaust gas inlet 32 and exhaust gas outlet 41. In this embodiment, exhaust gas inlet 32 and exhaust gas outlet 41 may comprise rib fittings or luer fittings. However, any type of fitting may be used without departing from the scope of the invention. Vacuum break device 26 may include generally hollow chamber 34. Chamber 34 may have one or more openings 30 which place the chamber in fluid communication with the atmosphere of the operating room.

In the illustrated embodiments, vacuum break device 26 has two openings 30 into chamber 34. More or less openings 30 may be provided without departing from the scope of the invention. The openings may have any shape including without limitation the arch shape illustrated in FIG. 1. The illustrated openings 30 are openings in the housing of vacuum break device 26. In alternative embodiments, a fluid conduit (either rigid or flexible) in fluid communication with chamber 34 may protrude from vacuum break device 26. For example, a tubing fitting could connect the chamber 34 to the atmosphere of the operating room either directly or through tubing. Tubing connected to such a fitting (not explicitly shown) may or may not have a valve within it.

In some embodiments, a filter may be included between openings 30 and the interior of chamber 34 to prevent particulates from flowing into chamber 34 and, in turn, into suction source 42. Such a filter may also prevent toxic gases or particulate matter from flowing from chamber 34 out into the operating room atmosphere through openings 30 if vacuum break device 26 malfunctions.

Vacuum break device 26 may include valve 31 to prevent smoke and other gases vented from the body cavity of patient 12 from flowing out through openings 30 into the atmosphere of the operating room when suction source 42 is not operational. In this embodiment, valve 31 comprises a rubber flapper valve which opens due to the force of suction source 42. In other embodiments, an umbrella valve may be used instead of or in addition to a rubber flapper valve. Any other type of suitable valve (or multiple valves) may be used to perform the function of valve 31. When suction source 42 is not operational, the resilient rubber valve (or the umbrella or other valve) closes openings 30 (or some other type of opening) and prevents or reduces the likelihood of smoke or gas vented from the body cavity of patient 12 from exiting into the atmosphere of the operating room. In embodiments where openings 30 comprise a fitting, tubing, or other fluid conduit between chamber 34 and the atmosphere of the operating room, a valve may be included within the tubing and/or the fitting for the same purpose.

As noted above, any number of openings and any shape of openings may be used without departing from the scope of the invention. In addition, the openings may be in any position on the housing of vacuum break device 26 without departing from the scope of the invention. In this embodiment, the openings are advantageously placed on a substantially flat circular face of vacuum break device 26 opposite exhaust gas outlet 41.

In preferred embodiments, the size, shape and configuration of openings 30 may be configured so as to reduce the omission of sound by vacuum break device 26. In addition, the openings 30 may be advantageously of sufficient size and number to minimize the pressure drop from the atmosphere of the operating room to chamber 34 within vacuum break device 26. Minimizing the pressure drop between the operating room atmosphere and chamber 34 of vacuum break device 26 minimizes the potential of the suction force generated by suction source 42 being felt within the body cavity of patient 12.

In some embodiments, vacuum break device 26 may include a flow guard 28 over one or more openings 30. In this embodiment, flow guard 28 is a rounded cage-like structure. Any type of flow guard structure may be used without departing from the scope of the invention. Flow guard 28 may be omitted without departing from the scope of the invention.

Flow guard 28 may be advantageously included on vacuum break device 26 to minimize the possibility of openings 30 becoming clogged during a surgical procedure. For example, because openings 30 experience a suction force from suction source 42, a surgical drape or other cloth material used during the surgery might be sucked against openings 30 such that the openings 30 become blocked. Blocking openings 30 may have the potential to injure the patient.

In some embodiments, vacuum break device 26 may include a condensation chamber 36. Condensation chamber 36 may comprise a drip chamber into which moisture may fall and be trapped as smoke and other gas evacuated from the body cavity of patient 12 travels through vacuum chamber 26. Condensation chamber 36 may simply be a part of chamber 34 that is positioned at a height below exhaust gas outlet 41. Condensation chamber 36 may be omitted without departing from the scope of the invention.

In this embodiment, exhaust gas outlet 41 is connected by tubing 40 to vacuum canister 38. Any type of connection between vacuum canister 38 and the fluid conduit between vacuum break device 26 and suction source 42 may be used without departing from the scope of the invention. In some embodiments, vacuum canister 38 may form a part of suction source 42. Vacuum canister 38 may be used to trap moisture and other solid particles which have traveled from the body cavity of patient 12 through vacuum break device 26. Using vacuum canister 38 to trap such particles may reduce maintenance of suction source 42. Conventional vacuum canisters typically used with medical suction systems may be used without departing from the scope of the invention. Vacuum canister 38 may be omitted without departing from the scope of the invention.

Suction source 42 may comprise any apparatus capable of generating a suctional force. Suction source 42 may comprise a portable suction source typically used in medical applications. In addition, suction source 42 may include a floor or wall mounted vacuum source such as is often found in an operating room of a hospital. Any other suction source may be used without departing from the scope of the invention.

In operation, smoke and other gases from the body cavity of patient 12 are transferred through an outlet port of trocar 14 controlled by stopcock 16 through a fluid flow path that includes vacuum break device 26. Once inside vacuum break device 26, suction source 42 sucks the smoke and other gases that were expelled from the body cavity of the patient into suction source 42. Thus, the amount of smoke and other gases expelled into the atmosphere of the operating room is minimized or eliminated. Vacuum break device 26 may protect the patient 12 from the force of suction source 42 by drawing air through openings 30 and maintaining the pressure of chamber 34 substantially near the pressure in the atmosphere of the operating room. Because little or no suctional force is felt within the body cavity of patient 12 or at the outlet of trocar 14, patient safety is increased by the invention. In addition, the lack of suctional force within the body cavity of patient 12 allows the body cavity to substantially remain inflated even while smoke and other gases are being vented through trocar 14. This aspect of the invention advantageously speeds the surgery.

FIG. 2 illustrates a second embodiment of vacuum break device 26 constructed in accordance with the invention. In this embodiment, a valve 31 controls flow through several openings (not explicitly shown) in the cover of vacuum break device surrounding post 52. A flange on valve 31 may be used to mount the valve to post 52 which has an opening to receive the flange. In this embodiment, another valve 56 controls the flow of gas through openings 30 in vacuum break device 26. In this embodiment, there are two triangular shaped openings. As discussed above, however, any number of openings and any shape of openings can be used without departing from the scope of the invention. Valve 56 comprises a cap mounted on spring 54. Spring 54 surrounds post 52 and may be mechanically or adhesively attached to either post 52 or to the cap of vacuum break device 26. The cap of valve 56 may surround and slide up and down relative to annulus 58.

In some embodiments, the annulus 58 containing openings 30 may have a small flange that engages with a flange on the inside of valve 56. This flange may be used to cause valve 56 to remain in a closed or substantially closed position without pressure being applied by the operator so long as the vacuum pressure within chamber 34 remains below a threshold. Vacuum pressure above the threshold may cause valve 56 to open as a safety measure to protect the patient. In some embodiments, an o-ring or gasket may allow for an integral seal between valve 56 and vacuum break device 26. In other embodiments guide rail type fixtures may be included to stabilize the valve 56 during up and down or side to side motion.

The operation of this embodiment is substantially similar to the embodiment described above except the inclusion of valve 56 provides an additional feature. In some cases, it is desirable to rapidly evacuate a body cavity during a surgical procedure. For example, when a large amount of smoke has built up and the doctor's vision is obstructed, it may be desirable to rapidly remove this smoke from the body cavity. Also, the conduit leading to exhaust gas inlet 32 (or exhaust gas inlet 32 itself) may become partially or completely blocked at times during a medical procedure due to condensation or debris lodging therein. The inclusion of valve 56 provides a method for addressing these issues.

When valve 56 is partially or completely closed (in this case by being depressed by an operator), the openings 30 into vacuum break device 26 are partially or completely obstructed. When a suction source is connected to exhaust gas outlet 41, the partial or complete closing of valve 56 should have the effect of increasing the vacuum pressure within chamber 34 of vacuum break device 26. This increase in pressure may reduce the ability of vacuum break device 26 to "break" the vacuum and allow the vacuum to be felt within the conduit leading to the body cavity and/or within the body cavity itself. Thus, valve 56 provides a way to temporarily increase the flow rate between the body cavity and vacuum break device 26. Spring 54 allows valve 56 to easily return to an open position when no longer depressed by the operator.

Thus, in some circumstances, medical personnel may desire to rapidly evacuate smoke by closing or partially closing valve 56, thus reducing the amount time waiting for smoke to clear. In other circumstances, medical personnel may clear an obstruction in the conduit between the body cavity and chamber 34 by closing or partially closing valve 56. In this embodiment, the triangular shaped openings 30 combined with the range of motion of valve 56 allow medical personnel to control how much the vacuum pressure and flow rate increases. If the flow rate is too high, there is a substantial loss of gas from the body cavity which can also delay the surgery. In addition, there is some risk that the abdomen could collapse onto sharp instruments leading to an injury to the patient. Thus, it is advantageous to use this embodiment with other valves and/or controlled size orifices with the conduit leading from the body cavity to vacuum break device 26 in order to minimize the risk of these potential problems. Valve 56 provides medical personnel with a way to quickly and easily obtain a brief increase in pressure and flow rate through the conduit leading to vacuum break device 26.

The use of valve 56 may allow the vacuum of the suction source to be felt (at least partially) within the body cavity. As discussed above, a flange (or some other mechanism) may allow valve 56 to remain in a closed (or partially closed) position without manual pressure being applied by an operator. In such circumstances, it is desirable to design valve 56 such that a vacuum over a certain threshold will automatically release valve 56. Thus, if the vacuum pressure exceeds a threshold, the valve may release automatically to reduce potential injury to the patient.

While one embodiment of valve 56 is illustrate in FIG. 2, other types of valves could be used for valve 56 without departing from the scope of the invention. For example a rotatable valve could rotate in a fashion such that depending upon the rotational position, all or a portion of openings 30 were obstructed. In an embodiment such as that shown in FIG. 1, a valve could be made to slide over openings 30 to partially or completely seal them. Such a valve could include a plate or other slidable member that slides (horizontally, vertically, or at any angle) to close partially or completely seal the openings. Such a valve could also be a plate or other rotatable member that rotates some amount to close partially or completely seal the openings. In some embodiments, the sliding plate (or other member) or rotating plate (or other member) can be spring loaded. Any type of valve which is capable of temporarily sealing openings 30 to increase vacuum pressure could be used without departing from the scope of the invention.

Although the present invention has been described in detail, it should be understood that various changes, substitutions and alterations can be made hereto without departing from the sphere and scope of the invention as defined by the appended claims.

To aid the Patent Office and any readers of any patent issued on this application and interpreting the claims appended hereto, Applicants wish to note that they do not intend any of the appended claims to invoke Paragraph 6 of 35 U.S.C. § 112 as it exists on the date of filing hereof unless "means for" or "step for" are used in the particular claim.

What is claimed is:

1. A method to vent gas from a body cavity during an endoscopic procedure, comprising:
    connecting a first conduit in fluid communication, either directly or indirectly, with the body cavity to an exhaust gas inlet of a vacuum break device, the vacuum break device comprising:
        a chamber,
        the chamber being both in fluid communication with the exhaust gas inlet and in fluid communication with an exhaust gas outlet,
        a first valve,
        wherein the chamber further comprises at least one opening in fluid communication with both the chamber and the atmospheric air where the endoscopic procedure is taking place and wherein the first valve is operable to at least partially obstruct the at least one opening resulting in an increase in gas flow rate within the first conduit due to increased vacuum pressure within the chamber; and
    connecting a second conduit in fluid communication with the exhaust gas outlet directly or indirectly to a suction source; and
    activating the suction source.

2. The method of claim 1, wherein the pressure between the body cavity and the chamber is maintained in the range of 1-20 mmHg.

3. The method of claim 1, wherein the pressure between the body cavity and the chamber is maintained in the range of 1-20 mmHg and the volumetric flow rate of the gas into the exhaust gas inlet is between 1 and 20 liters per minute.

4. The method of claim 1, wherein the first conduit further comprises a second valve operable to regulate the flow of gas through the first conduit.

5. The method of claim 1, wherein the second conduit further comprises a second valve operable to regulate the flow of gas through the second conduit.

6. The method of claim 1, further comprising:
    connecting a suction canister directly or indirectly to the second conduit.

7. The method of claim 1, further comprising:
    placing a dessicant in a fluid flow path between the body cavity and the vacuum break device.

8. The method of claim 1, further comprising:
    placing a dessicant in a fluid flow path between the vacuum break device and the suction source.

9. The method of claim 1, wherein the first conduit further comprises an orifice operable to regulate the flow of gas through the first conduit.

10. The method of claim 1, wherein the vacuum break device further comprises a second valve operable to cause the at least one opening to be in fluid communication with the atmospheric air when the suction source is operational and to substantially prevent gas flow through the opening when the suction source is not operational.

11. The method of claim 1, wherein the vacuum break device further comprises a condensation trap.

12. The method of claim 1, further comprising removing condensate from the first conduit by at least partially closing the first valve.

13. The method of claim 1, wherein the first valve is operable to release from its closed position absent pressure from an operator when the vacuum pressure within the chamber exceeds a threshold.

* * * * *